United States Patent
Lev et al.

(10) Patent No.: US 11,486,868 B2
(45) Date of Patent: Nov. 1, 2022

(54) AUTOMATIC PARTICLE OR SCENT TRACING TO CHECK SOCIAL DISTANCING IN PUBLIC PLACES

(71) Applicant: NEC Corporation Of America, Herzlia (IL)

(72) Inventors: Tsvi Lev, Tel-Aviv (IL); Yaacov Hoch, Ramat-Gan (IL)

(73) Assignee: NEC Corporation Of America, Herzlia (IL)

( * ) Notice: Subject to any disclaimer, the term of this patent is extended or adjusted under 35 U.S.C. 154(b) by 56 days.

(21) Appl. No.: 17/076,944

(22) Filed: Oct. 22, 2020

(65) Prior Publication Data

US 2022/0128535 A1 Apr. 28, 2022

(51) Int. Cl.
| | |
|---|---|
| *A62B 7/10* | (2006.01) |
| *G01N 33/00* | (2006.01) |
| *G08B 21/18* | (2006.01) |
| *A41D 1/00* | (2018.01) |
| *A41D 13/11* | (2006.01) |
| *A62B 18/02* | (2006.01) |
| *A62B 18/08* | (2006.01) |
| *A41D 31/00* | (2019.01) |
| *A62B 23/02* | (2006.01) |

(52) U.S. Cl.
CPC .......... *G01N 33/0063* (2013.01); *A41D 1/002* (2013.01); *A41D 13/11* (2013.01); *A41D 31/00* (2013.01); *A62B 18/025* (2013.01); *A62B 18/08* (2013.01); *G01N 33/0075* (2013.01); *G08B 21/182* (2013.01); *A62B 23/02* (2013.01)

(58) Field of Classification Search
CPC .......... G01N 33/0063; G01N 33/0075; A41D 1/002; A41D 13/11; A41D 31/00; A62B 18/025; A62B 18/08; A62B 23/02; G08B 21/182
See application file for complete search history.

(56) References Cited

U.S. PATENT DOCUMENTS

| | | | |
|---|---|---|---|
| 5,243,708 | A | 9/1993 | Vanuch |
| 5,538,013 | A | 7/1996 | Brannon |

(Continued)

FOREIGN PATENT DOCUMENTS

KR 10-2019-0005355 1/2019

OTHER PUBLICATIONS

Amazon "Health Innovative Airbliss Air Pollution Menthol Face Mask With Fresh Fragrance", Amazon (Home & Kitchen), Product Description, p. 1-3, 2020.

(Continued)

*Primary Examiner* — Hongmin Fan

(57) ABSTRACT

A kit includes at least one facemask configured to cover a respective user's mouth and nose. The facemask contains at least one layer impregnated with a first chemical. When the facemask covers the respective user's mouth and nose, airborne particles of the first chemical are released from the at least one layer through the user's breathing. A sensor is configured to measure airborne concentration of the first chemical. A processing circuitry is configured to receive outputs of the sensor, to calculate a change in airborne concentration of the first chemical, and to issue a notification when the airborne concentration of the first chemical increases at above a predetermined rate.

19 Claims, 6 Drawing Sheets

(56) References Cited

U.S. PATENT DOCUMENTS

| | | | |
|---|---|---|---|
| 6,244,265 | B1 | 6/2001 | Cronk et al. |
| 7,707,655 | B2 | 5/2010 | Braunecker et al. |
| 8,316,850 | B2 * | 11/2012 | Grilliot .................... A62B 7/02 |
| | | | 128/204.26 |
| 9,855,360 | B2 | 1/2018 | Broyles et al. |
| 2005/0142966 | A1 * | 6/2005 | Quincy, III ........ B01D 39/1623 |
| | | | 442/72 |
| 2011/0297152 | A1 | 12/2011 | Duveen et al. |
| 2012/0144556 | A1 | 6/2012 | Fiebel et al. |
| 2014/0237695 | A1 | 8/2014 | Al Malki |
| 2016/0121144 | A1 * | 5/2016 | Hyde .................. A62B 23/025 |
| | | | 128/206.17 |
| 2019/0145874 | A1 * | 5/2019 | Woolsey .............. G01N 1/4022 |
| | | | 73/863.12 |

OTHER PUBLICATIONS

De Vries et al. "Early Detection of Lung Cancer in Patients With COPD by eNose Technology", European Respiratory Journal, 52(Suppl. 62): #PA1760, 2020.

Doughty et al. "Automated Aerosol Raman Spectrometer for Semi-Continuous Sampling of Atmospheric Aerosol", Journal of Quantitative Spectroscopy & Radiative Transfer, 188: 103-117, Available Online Jul. 5, 2016.

EU Science Hub "Measuring Air Pollution With Low-Cost Sensors. Thoughts on the Quality of Data Measured by Sensors", European Commission, Science Hub, p. 1-4, 2020.

Fenelly "Particle Sizes of Infectious Aerosols: Implications for Infection Control", The Lancet Respiratory Medicine, 8(9): 914-924, Published Online Jul. 24, 2020.

Fronczek et al. "Biosensors for Monitoring Airborne Pathogens", Journal of Laboratory Automation, 20(4): 390-410, Published Online Apr. 10, 2015.

Gralton et al. "The Role of Particle Size in Aerosolised Pathogen Transmission: A Review", Journal of Infection, 62(1): 1-13, Available Online Nov. 19, 2010.

Henneberry "How Surgical Masks Are Made", Thomas Publishing Company, p. 1-8, Modified Nov. 1, 2020.

Jung et al. "Advanced Design of Fiber-Based Particulate Filters: Materials, Morphology, and Construction of Fibrous Assembly", Polymers, 12(8): 1714-1-1714-23, Published Online Jul. 30, 2020.

Lattanzio "Particulate Matter Sensing for Air Quality Measurements", Sensirion, The Sensor Company, p. 1-5, 2020.

Milton et al. "Influenza Virus Aerosols in Human Exhaled Breath: Particle Size, Culturability, and Effect of Surgical Masks", PLOS ONE Pathogens, 9(3): e1003205-1-e1003205-7, Published Online Mar. 7, 2013.

Nanyang Technology University "Airborne Chemicals Instantly Identified Using New Technology", ScienceDaily, Nanyang Technology University, Singapore, NTU Singapore, p. 1-3, Oct. 15, 2019.

Phan-Quang et al. "Tracking Airborne Molecules From Afar: Three-Dimensional Metal-Organic Framework-Surface-Enhanced Raman Scattering Platform for Stand-Off and Real-Time Atmospheric Monitoring", ACS Nano, 13(10): 12090-12099, Published Online Sep. 13, 2019.

Skwarecki "Why You Can Smell a Fart Through a Mask", Lifehacker, p. 1-13, Jul. 22, 2020.

Smith "The Science and Tech of Face Masks", Medium, Blog, 16 P., Apr. 27, 2020.

Tellier "Review of Aerosol Transmission of Influenza A Virus", Emerging Infectious Diseases, 12(11): 1657-1662, Nov. 2006.

Verreault et al. "Methods for Sampling of Airborne Viruses", Microbiology and Molecular Biology Reviews, 72(3): 413-444, Sep. 2008.

Wilson et al. "Applications and Advances in Electronic-Nose Technologies", Sensors, 9(7): 5099-5148,Published Online Jun. 29, 2009.

Zhou et al. "Airborne Particles Detection and Sizing at Single Particle Level by a Novel Electrical Current Pulse Sensor", Measurement, 92: 58-62, Available Online Jun. 8, 2016.

* cited by examiner

AUTOMATIC PARTICLE OR SCENT TRACING TO CHECK SOCIAL DISTANCING IN PUBLIC PLACES

FIELD AND BACKGROUND OF THE INVENTION

The present invention, in some embodiments, relates to a kit for detecting the presence of exhaled airborne particles in a public place, and more specifically, but not exclusively, to a mask impregnated with a substance that adheres to exhaled aerosol droplets and to a detector for detecting airborne concentration of the substance.

The COVID-19 pandemic has cast worldwide attention onto prevention of disease transmission. In particular, certain viruses, such as influenza and possibly the novel coronavirus, are spread through airborne transmission. In airborne transmission, the virus adheres to aerosol droplets formed during breathing or coughing. These aerosol droplets are 5 µm or smaller in size. The aerosol droplets disperse through the air and carry the virus with them.

It is also known that different types or forces of exhaling causes a wider spread of airborne aerosol particles. For example, singing, shouting, or talking loudly all cause a greater formation of airborne aerosol particles than breathing, and thus cause a greater risk of disease transmission. In addition, some individuals emit airborne particles at a rate more than an order of magnitude larger than their peers. Such individuals, who are called "superemitters" or "superspreaders," may pose a risk of airborne disease transmission even at a reduced speech volume.

One widespread technique for reducing the risk of airborne transmission involves the wearing of masks. The mask includes a filter layer that is designed to permit breathing therethrough, while reducing or eliminating the transmission of particles through the mask. Masks have been shown to be highly effective at preventing transmission of large droplets (larger than 5 µm), such as those generated through sneezing, and more moderately effective at preventing transmission of aerosol droplets.

For example, one study examined the exhaled breath of influenza patients both when they were wearing a surgical mask and when they were not wearing a surgical mask. Milton, Donald K et al. "Influenza virus aerosols in human exhaled breath: particle size, culturability, and effect of surgical masks." *PLoS pathogens* vol. 9,3 (2013): e1003205. doi:10.1371/journal.ppat.1003205. For exhaled aerosol fractions larger than 5 µm, the study detected influenza virus RNA in 11% of patients wearing surgical masks, and in 43% of patients not wearing masks. For patients wearing masks, the total number of airborne virus copies present in the exhaled air was reduced by 25 fold. By contrast, for fine particle samples smaller than 5 µm, the study detected influenza virus RNA in 78% of patients wearing masks, and in 92% of patients not wearing masks. The facemasks caused a 2.8 fold reduction in the number of airborne virus copies present in the exhaled air.

Masks have been used for various medical and aesthetic purposes other than prevention of disease transmission. One function of masks has been to provide a pleasant scent in order to counteract the effects of an ill-smelling environment. For example, the mask may be impregnated with menthol, with furaneol, or with another chemical that emits a soothing scent. When the user breathes normally while wearing the mask, he or she inhales the scent, which overpowers the environmental odors.

SUMMARY OF THE INVENTION

As the study cited above demonstrates, while masks have been shown to be effective at preventing airborne transmission of viruses, they have more limited utility for preventing airborne transmission via small aerosol particles. In addition, in a pandemic scenario in which people are wearing masks in a public setting, without medical supervision, the masks are likely even less effective at preventing airborne transmission. This is because not every person wears the mask properly, whether intentionally or otherwise. In addition, not every person wears a surgical mask with a filter, rendering the masks less effective at preventing transmission of airborne particles. As a result, public spaces, especially those with heavy human traffic, may have a significant number of airborne aerosol particles carrying viruses.

To determine whether a public space is safe, the best analytical technique would be to measure airborne concentration of the virus itself. However, currently available technology for measuring airborne transmission of viruses is expensive and impractical for widespread implementation. It is challenging to provide a sampling substrate that collects virus material from the air. Furthermore, even if a reliable sampling substrate is used, the amount of virus material that is present in sampled air is typically extremely small, and it must be amplified through polymerase chain reactions (PCR) in order to be identified and measured. PCR is an expensive process involving machinery that is typically used only in a laboratory.

Accordingly, a need exists for a reliable, low-cost diagnostic technique for evaluating the concentration of exhaled aerosol particles, which can be used to gauge the safety of air in public spaces.

The present disclosure, in some embodiments, addresses this need through the use of a mask impregnated with a chemical. The chemical is dislodged from the mask during a user's breathing. The chemical may have a pleasant odor or it may be odorless. The chemical may be a particulate solid, or a volatile liquid, or a gas. Unlike scented masks whose purpose is to release odor-producing particles into a user's nose, the purpose of the mask according to the disclosed embodiments is to produce airborne chemicals that are spread through the user's breath. The airborne particles are spread, notwithstanding the presence of the mask, either through the filter of the mask, or through gaps between the mask and the user's skin. A sensor is placed in a location in a room where the user is located. The sensor measures airborne concentration of the chemical. The sensor may utilize one or more of gas chromatography, mass spectrometry, Raman spectroscopy, time of flight analysis, electrical current pulse sensing, electrochemical sensing, metal oxide sensing, laser scattering, photoionization, or optical particle counting.

According to a first aspect, a kit is disclosed. The kit includes at least one facemask configured to cover a respective user's mouth and nose. The at least one facemask contains at least one layer impregnated with a first chemical. When the at least one facemask covers the respective user's mouth and nose, airborne particles of the first chemical are released from the at least one layer through the user's breathing. A sensor is configured to measure airborne concentration of the first chemical. A processing circuitry is configured to receive outputs of the sensor, to calculate a change in airborne concentration of the first chemical, and to issue a notification when the airborne concentration of the first chemical increases at above a predetermined rate. The increase of airborne concentration of the first chemical serves as a proxy for the dispersal of one or more users' breath, and thus indicates whether a detectable concentration of exhaled breath is present in the room. This, in turn, may be used to assess the safety of the room.

In another implementation according to the first aspect, the first chemical adheres to exhaled aerosol droplets with a diameter less than 5 μm. For example, the first chemical may be a finely particulate solid or a liquid that forms microdroplets. Advantageously, the distribution pattern of the first chemical thus approximates the distribution pattern of an airborne virus.

In another implementation according to the first aspect, the first chemical is odorless to the human olfactory system. In another implementation according to the first aspect, the first chemical emits an odor that is recognizable to the human olfactory system at concentrations above an odor detection threshold, and is impregnate at a sufficiently low concentration such that the airborne particles are released from the at least one facemask at a concentration below the odor detection threshold. Advantageously, while it is possible to use a first chemical that emits a pleasant scent, it is not necessary to do so, because the chemical is to be detected by an analytical sensor rather than the human nose. The mask may thus be mass-distributed without concern as to whether users like or dislike any particular scent.

In another implementation according to the first aspect, the first chemical is a monosaccharide, a disaccharide, a polysaccharide, or a sugar alcohol. Advantageously, these chemicals are odorless, safe to ingest, and inexpensive, may be formed as small particles, and may be detected with various analytical sensors.

In another implementation according to the first aspect, the sensor is configured to measure airborne concentration of the first chemical based on one or more of gas chromatography, mass spectrometry, Raman spectroscopy, time of flight analysis, electrical current pulse sensing, or laser scattering. Advantageously, these techniques are effective for measuring airborne concentration of particulate, liquid, or gaseous matter.

In another implementation according to the first aspect, a patch impregnated with a second chemical is attachable to the user's clothing or body. When the patch is worn by the user, the sensor is configured to measure airborne concentration of the second chemical. The processing circuitry is configured to issue the notification only when the airborne concentration of the first chemical increases at a rate that exceeds the increase in concentration of the second chemical by a predetermined value.

Advantageously, the detection of the second chemical may be used to cancel out any environmental effects causing increased air circulation, such as a strong ventilation system. As a result, the effect of the increased concentration of the first chemical due to the user's breathing may be isolated.

In another implementation according to the first aspect, the sensor is installed in a location having a delineated space for user movement, at a predetermined distance from said delineated space. For example, the sensor may be installed on a ceiling, at an air vent, or above a closet. Requiring a minimum distance between a user and a sensor prevents a false positive resulting from the user's breathing directly onto the sensor.

In another implementation according to the first aspect, a motion sensor or optical sensor is configured to determine a number of users in a room. The processing circuitry is configured to set the predetermined rate based on the number of users. Thus, in addition to determining whether any particular room has exceeded a minimum concentration of airborne particles, or has increased its concentration at a particular rate, the processing circuitry may also determine whether the increase in concentration is in line with expectations based on the number of users in the room. If the increase in concentration is abnormally high, this may be a sign that one or more of the users is not wearing the mask correctly, or that the user is a super-spreader due to his or her manner of speaking or exhaling.

In another implementation according to the first aspect, the notification includes an instruction to the user to adjust a fit of the at least one facemask. In another implementation according to the first aspect, the notification includes an instruction to the user to modulate a loudness of vocalization or a force of exhaling. The notification may thus include instructions for corrective activities to limit spread of exhaled airborne particles.

According to a second aspect, a method is disclosed. The method comprises measuring airborne concentration of a first chemical. The first chemical is released from at least one layer of at least one facemask impregnated with said first chemical due to a respective user's breathing when wearing the at least one facemask. The method further comprises calculating a change in airborne concentration of the first chemical, and issuing a notification when the airborne concentration of the first chemical increases at above a predetermined rate. The increase of airborne concentration of the first chemical serves as a proxy for the dispersal of one or more users' breath, and thus indicates whether a detectable concentration of exhaled breath is present in the room. This, in turn, may be used to assess the safety of the room.

In another implementation according to the second aspect, the first chemical adheres to exhaled aerosol droplets with a diameter less than 5 μm. For example, the first chemical may be a finely particulate solid or a liquid that forms microdroplets. The measuring step comprises measuring airborne concentration of aerosolized particles of the first chemical. Advantageously, measuring the distribution pattern of the first chemical thus approximates measuring the distribution pattern of an airborne virus.

In another implementation according to the second aspect, the measuring step comprises measuring airborne concentration of the first chemical based on one or more of gas chromatography, mass spectrometry, Raman spectroscopy, time of flight analysis, electrical current pulse sensing, or laser scattering. Advantageously, these techniques are effective for measuring airborne concentration of particulate, liquid, or gaseous matter.

In another implementation according to the second aspect, the method further comprises measuring airborne concentration of a second chemical. The second chemical is impregnated on a patch that is attachable to the user's clothing or body. The method further comprises calculating a change in airborne concentration of the second chemical, and issuing the notification only when the airborne concentration of the first chemical increases at a rate that exceeds the increase in concentration of the second chemical by a predetermined value. The detection of the second chemical may be used to cancel out any environmental effects causing increased air circulation, such as a strong ventilation system. As a result, the effect of the increased concentration of the first chemical due to the user's breathing may be isolated.

In another implementation according to the second aspect, the measuring step is performed at a predetermined minimum distance from a delineated space for user movement.

For example, the measuring step may be performed by a sensor installed on a ceiling, at an air vent, or above a closet. Requiring a minimum distance between a user and a sensor prevents a false positive resulting from the user's breathing directly onto the sensor.

In another implementation according to the second aspect, the method further comprises determining a number of users in a room with a motion sensor or optical sensor, and setting the predetermined rate based on the number of users. Thus, the method may also be used to determine whether the increase in concentration is in line with expectations based on the number of users in the room. If the increase in concentration is abnormally high, this may be a sign that one or more of the users is not wearing the mask correctly, or that the user is a super-spreader due to his or her manner of speaking or exhaling.

In another implementation according to the second aspect, the step of issuing a notification comprises instructing the user to adjust a fit of the at least one facemask. In another implementation according to the second aspect, the step of issuing a notification comprises instructing the user to modulate a loudness of vocalization or a force of exhaling. The notification may thus include instructions for corrective activities to limit spread of exhaled airborne particles.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
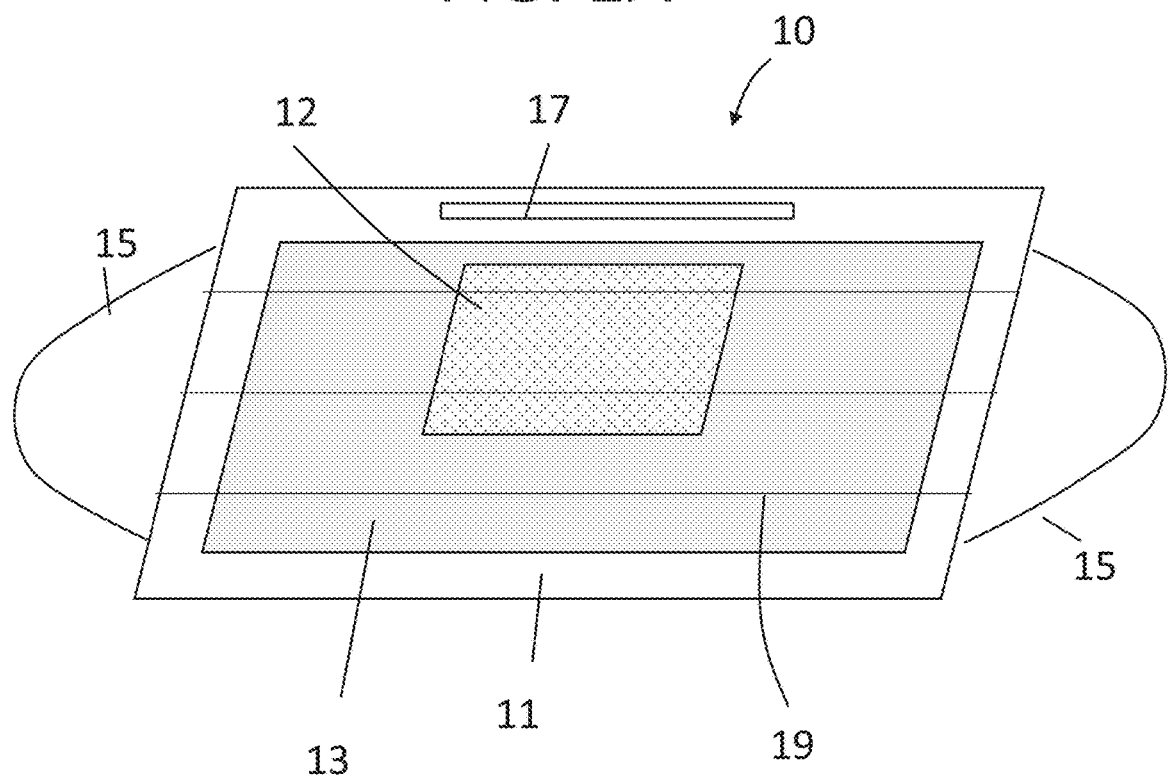
FIG. 1A is a schematic depiction of a surgical mask impregnated with a chemical, according to embodiments of the present disclosure.

The present invention, in some embodiments, relates to a kit for detecting the presence of exhaled airborne particles in a public place, and more specifically, but not exclusively, to a mask impregnated with a substance that adheres to exhaled aerosol droplets and to a detector for detecting airborne concentration of the substance.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1B:
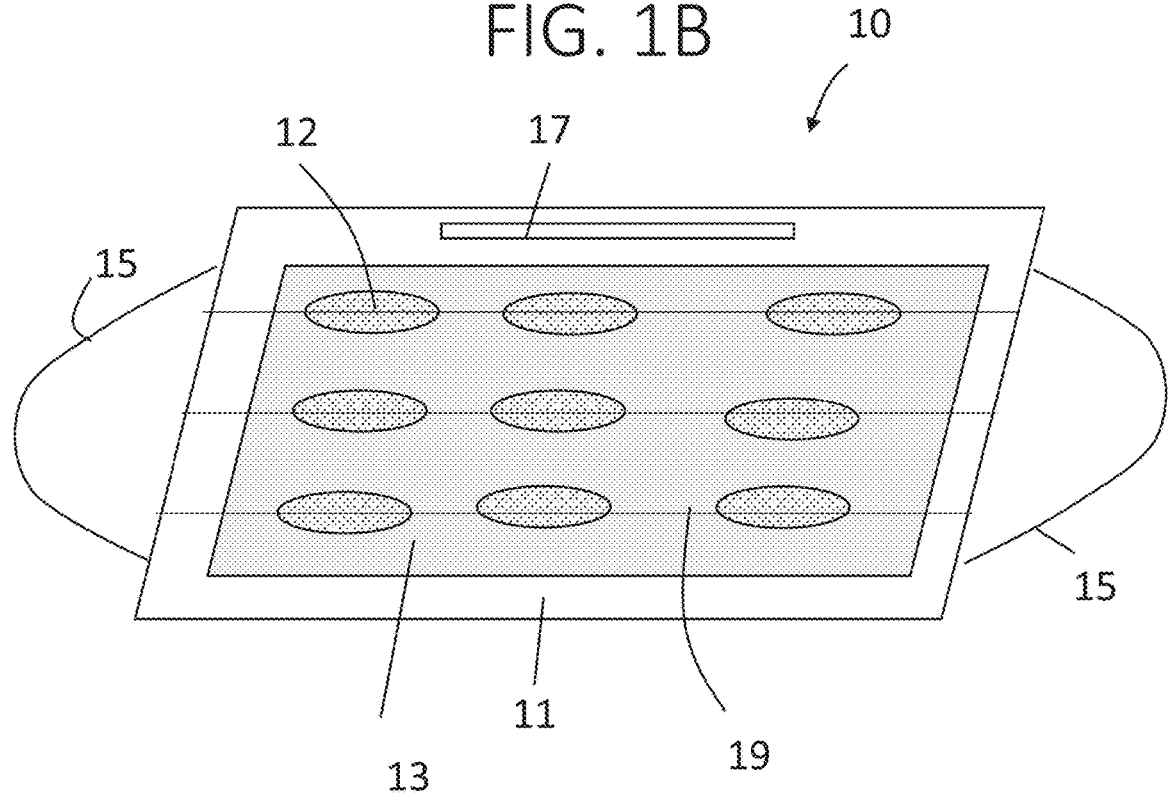
FIG. 1B is a schematic depiction of a second embodiment of a surgical mask impregnated with a chemical, according to embodiments of the present disclosure.
Figure 2:
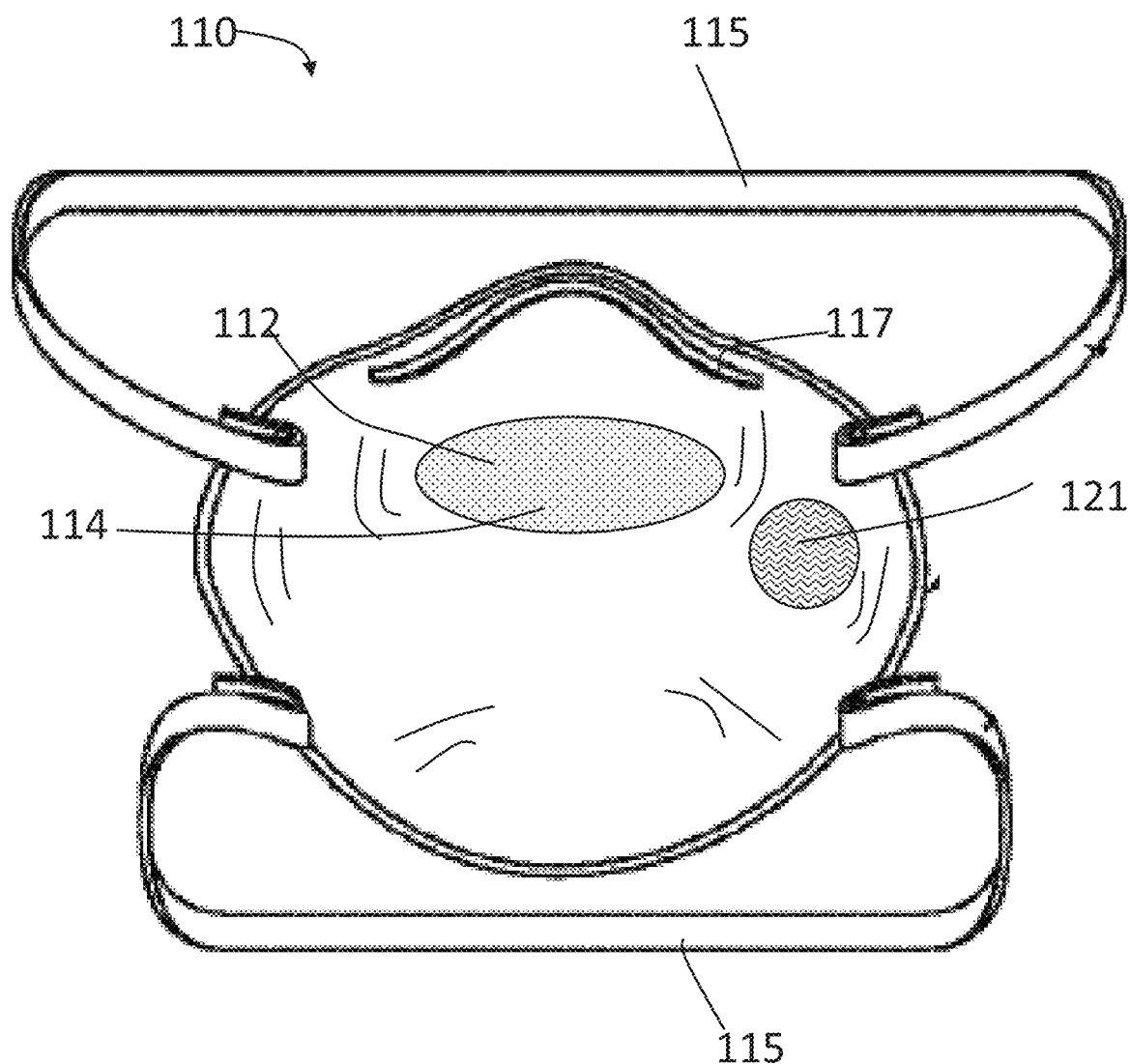
FIG. 2 is a schematic depiction of a filter mask impregnated with a chemical, according to embodiments of the present disclosure.

FIGS. 1A, 1B, and 2 depict various embodiments of a facemask 10, 110 that is impregnated with a first chemical 14, 114. In the present disclosure, the terms "mask" and "facemask" are used interchangeably. Facemask 10, 110 is shaped and sized to be worn over a user's mouth and nose. In the embodiment of FIGS. 1A and 1B, facemask 10 is a surgical mask. Facemask 10 includes ear loops 15, which are used to retain the facemask 10 on the user's face, and an aluminum or memory metal strip 17, which is bendable to fit over a bridge of the user's nose. Facemask 10 includes pleats 19, which are closed prior to use, for easy packaging of the facemask, and which are opened when worn on the user's face.

Standard medical-grade surgical masks typically have three layers, or plies. The outer layer is a waterproof synthetic fabric. The outer layer, illustrated in FIGS. 1A and 1B as layer 11, traps against watery sneezes and coughs, and traps large particles on which bacteria and viruses often travel. It also protects against splashes of blood or other bodily fluids during procedures. The middle layer, not shown in FIGS. 1A and 1B, is typically a 1 micron filter, although filters have been used in surgical facemasks that filter as low as 0.1 microns. The most interior layer, shown in FIGS. 1A and 1B as layer 13, is another filter that absorbs vapor from the user's own breath. The internal and external layers 11, 13 are typically made with non-woven fabric, which has better bacteria filtration and air permeability while remaining less slippery than woven cloth. The material most commonly used to make them is polypropylene. Rayon, polyester, polyurethane, and polyethylene may also be used.

The facemask may also be a respirator mask 110, as depicted in the embodiment of FIG. 2. Respirator masks are typically made of polypropylene. Respirator mask 110 may be of any filtering efficiency, such as N95, KN95, or N99. Respirator mask 110 includes elastics 115, which are attached snugly to back of the user's head to prevent entry of airborne particles beyond the mask. Aluminum or memory metal strip 117 is bendable to secure the facemask 110 around the user's nose. A one-way filter 121 is incorporated into the body of the facemask 110 to allow the venting of exhaled air without destroying the airtight seal.

Facemask 10, 110 may comply with all applicable safety standards for medical facemasks, such as ASTM standards F2101, EN14683, F2299, F1862, and F1671.

Facemask 10, 110 includes at least one layer 12, 112 that is impregnated with a first chemical 14, 114. When the facemask 10 is constructed of multiple plies, the layer 12 may be an additional ply that is in between the innermost and outermost layers. An advantage of this configuration is that it allows the use of first chemicals that might potentially be irritating if left in contact with the face for a long period of time. Layer 12, 112 may also be attached to the side of the innermost layer that faces the face.

In the embodiment of FIG. 1A and FIG. 2, layer 12 or 112 is a single, contiguous structure. In the embodiment of FIG. 1B, layer 12 is spread out into multiple structures, along the area of facemask 10. In a particularly advantageous embodiment, layer 12 is a series of scent patches that are sealed when pleats 19 of the mask 10 are folded, and which are opened when the pleats 19 are spread out. An exemplary construction of such scent patches is described in U.S. Pat. No. 10,486,001, the contents of which are incorporated by reference as if fully set forth herein. An advantage of this embodiment is that the chemical 14 is retained sealed within the pleat 19 folds until the mask is worn, without requiring an additional wrapper for the facemask 10.

First chemical 14 may be any chemical that is safe for inhalation and is detectable using analytical techniques for detecting airborne chemicals. First chemical 14 may be a solid, a liquid, or a gas.

In one embodiment, first chemical 14 is an essential oil. As used in the present disclosure, an essential oil is any of a class of volatile oils principally obtained from plants, possessing the odor and other characteristic properties of the plant, used chiefly in the manufacture of perfumes, flavors, and pharmaceuticals. However, the essential oil may also be synthetically manufactured. Non-limiting examples of such essential oils include menthol, camphor, orange, lavender, peppermint, geraniol, citronella, rose oil, lemon oil, and sandalwood.

Many essential oils are currently impregnated in medical products such as masks, nasal strips, or wearable patches. These essential oils are selected because they provide a pleasant or calming scent. These essential oils may be absorbed in a base oil layer that slowly releases the essential oil, or another slow-release mechanism may be employed, such that the essential oil may be inhaled over an extended period of time, such as several hours. Examples of such slow release mechanisms may be found, inter alia, in U.S. Pat. Nos. 10,486,001, 9,855,360; 8,506,996, and 6,244,265, the contents of which are incorporated by reference as if fully set forth herein. Such delivery mechanisms include, but are not limited to, fixatives, gels, starches, carriers, porous hydrophilic inorganics, micro-capsules, cellulosic carriers, cyclodextrine coatings and body-activated coatings, such as those which release fragrant oils upon achieving a certain temperature, reaching a certain pH, or, when they come in contact with liquid perspiration. When the first chemical 14 is an essential oil, layer 12 may include such delivery mechanisms.

In the foregoing examples, as mentioned above, the essential oils are selected because they cause a physiological effect, such as a pleasant scent or a soothing or cooling sensation. As a result, the essential oils are impregnated in the medical product at a sufficiently high concentration to produce this physiological effect. For example, if the physiological effect is production of a pleasant scent, the concentration of the essential oil is selected so that the generated scent would be sufficiently above the odor detection threshold. As used in the present disclosure, the term "odor detection threshold" refers to is the lowest concentration of a certain odor-generating compound that is perceivable by the human sense of smell. In embodiments of the present disclosure, however, it is not necessary to generate any physiological effect. So long as the airborne concentration of the first chemical 14 is detectable, the mask 10 may be used to evaluate a user's breathing. Indeed, a physiological effect could be counterproductive, insofar as not every user would be interested in experiencing such a physiological effect, and accordingly would refrain from wearing the mask 10. Accordingly, in embodiments of the present disclosure, the first chemical is odorless, or it is impregnated at a sufficiently low concentration such that airborne particles are released from the facemask 10 at a concentration below the odor detection threshold.

In some embodiments, the first chemical 14 is a finely particulate solid. In particular, the first chemical 14 may be usable as an excipient. An excipient is a substance formulated alongside the active ingredient of a medication, included for the purpose of long-term stabilization, or for other non-therapeutic purposes. Excipients are typically selected for their lack of taste or odor at room temperature. In some embodiments, the first chemical 14 is a monosaccharide, a disaccharide, a polysaccharide, or a sugar alcohol. Examples of monosaccharides are glucose, fructose, and galactose; examples of disaccharides are sucrose, lactose and maltose; and examples of sugar alcohols are sorbitol and mannitol. The first chemical may also be a starch such as amylose or amylopectine, or a sugar substitute such as aspartame. These compounds are solid and odorless at room temperature. Another advantage of these chemicals is that certain sugars are commercially available in powdered form, with granules having a size of approximately 50 µm. In addition, these chemicals are detectable using various analytical techniques. For example, Raman spectroscopy is used in medical practice to detect concentrations of glucose.

In some embodiments, the first chemical 14 adheres to aerosol droplets with a diameter of less than 5 µm. For example, the first chemical may be hydrophilic or may be water soluble. Advantageously, in such embodiments, the first chemical spreads in the air using the same mechanism as an airborne virus. In other embodiments, the first chemical 14 does not adhere to aerosol droplets. Nevertheless, the distribution of the first chemical in the air serves as a suitable proxy or estimate for how many exhaled aerosol droplets are distributed in the air.

Figure 3:
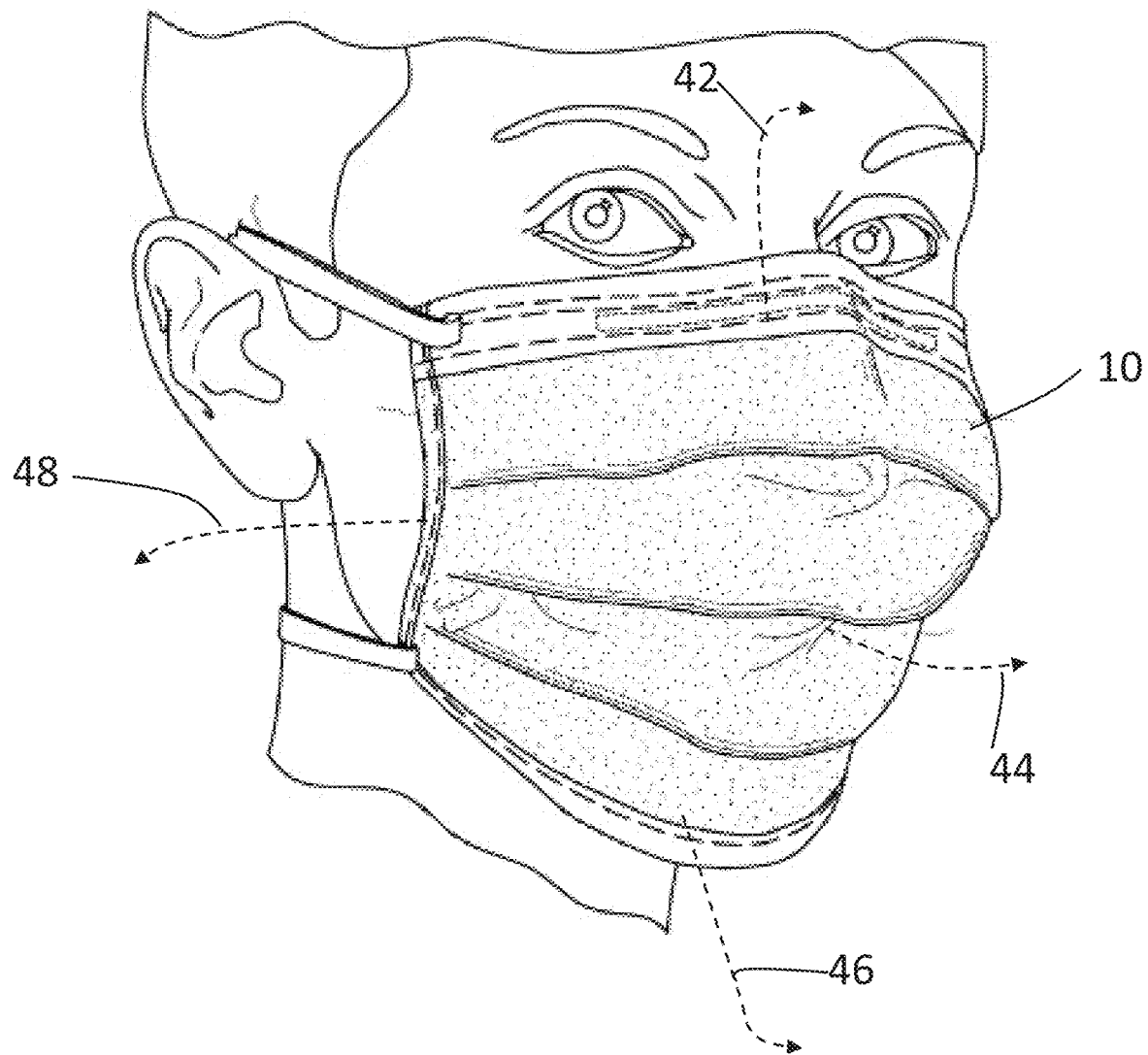
FIG. 3 is a schematic depiction of airborne particles of the chemical exiting the area between the mask and the user's face, according to embodiments of the present disclosure.

FIG. 3 schematically illustrates a process for distribution of the first chemical 14 in an environment. As shown in FIG. 3, a user is wearing mask 10. The filter layers of the mask are designed to at least partially prevent transmission of the first chemical 14 through the space between the face and the mask 10. However, if the particles of the first chemical 14 are sufficiently small, a percentage of airborne particles of the first chemical may pass through the layers of the mask, as illustrated with arrow 44. As used in the present disclosure, the term "airborne particles" includes particles in the solid, liquid, and gaseous phases. In addition, airborne particles of the first chemical 14 may pass through gaps between the mask 10 and the user's face, such as through gaps 42, 46, and 48. Because the mask is not airtight, the distribution of the first chemical 14 into the environment is thus expected, even when the user is breathing normally and the mask is being worn properly. Environmental conditions in the user's location also influence the rate of distribution of the first chemical 14. However, certain user activities may cause the distribution of the first chemical into the environment to increase more rapidly than expected. These activities may include breathing heavily, talking loudly, or singing. Such activities cause increased formation of aerosol droplets, which may bind to the first chemical 14 and carry the first chemical 14 out of the mask 10. In addition, such activities may cause the user to exhale more forcefully, causing more air and airborne particles to exit the space between the face and the mask 10 and enter the environment. In addition, the user may wear the mask incorrectly, resulting in a larger space between the mask 10 and the user's face, which would cause an additional increase in airborne concentration of the particles.

Figure 4:
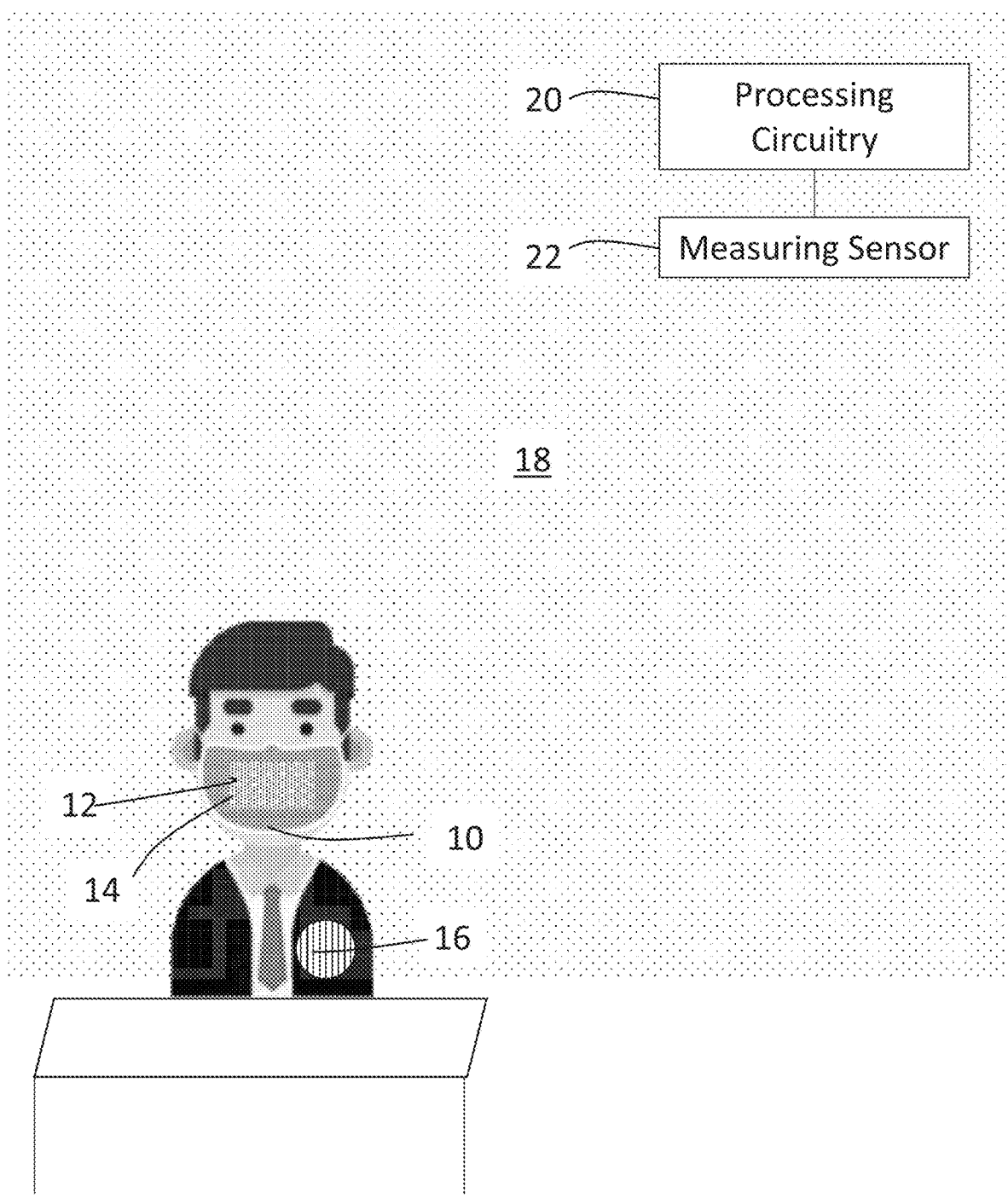
FIG. 4 is a schematic depiction of a system for automatic tracing of exhaled particles with a single user, according to embodiments of the present disclosure.

FIG. 4 illustrates different components of a kit for measuring a rate of increase of exhaled airborne particles, with a single user. The kit includes at least one facemask 10, processing circuitry 20, and measuring sensor 22.

The kit optionally includes patch 16. In the illustrated embodiment, patch 16 is attached to the user's clothing. However, patch 16 may also be placed anywhere within the environment. Patch 16 is impregnated with a second chemical. The second chemical is different than first chemical 14, but may have similar chemical properties. For example, the size and volatility of the first and second chemicals may be similar, so that they are distributed in the environment at the same rate. The patch 16 is placed at a location such that it is spread through the environment solely through the circulation of air within the environment, without being influenced by the user's breathing.

The measuring sensor 22 is used to measure the airborne concentration of the first chemical and the second chemical. Airborne particles of the first chemical 14 in the environment are schematically represented by dots 18.

Measuring sensor 22 may use any suitable analytical technique for measuring airborne concentration of an airborne particulate solid, volatile liquid, or gas. For example, the measuring sensor may include one or more of the following analytical techniques: gas chromatography, mass spectrometry, Raman spectroscopy, time of flight analysis, electrical current pulse sensing, or laser scattering. These techniques, and others, are discussed below.

Gas chromatography and mass spectrometry (GCMS) are long-established and widely used analytical techniques for identifying and measuring chemicals, especially smaller and more volatile chemicals. GC-MS is currently used for detection of fine airborne particulate matter, such as pesticides. Aerosol mass spectrometry is a particular type of mass spectrometry used to detect aerosol particles.

Raman spectroscopy is another long-established analytical technique. Raman spectroscopy has been used to determine the composition of atmospheric aerosols, including particles containing black carbon, organic carbon, and inorganic materials, as well as desert dust, sea spray, and oceanic aerosols. Recent advances in Raman spectroscopy have enabled automated trapping of airborne particles and semi-continuous Raman spectroscopy of these trapped particles.

Time of flight analysis, also known as LIDAR (light detecting and ranging), may be used to determine properties of airborne particles. A typical LIDAR sensor emits pulsed light waves into the surrounding environment. These pulses bounce off surrounding objects and return to the sensor. The sensor uses the time it took for each pulse to return to the sensor to calculate the distance it traveled. LIDAR devices have been used to characterize particulate matter and airborne aerosols, such as desert dust. This characterization is based on the principle that information from the atmospheric structure and constituents can be obtained from how the laser light transmitted into the atmosphere interacts with the atmosphere and is backscattered by various targets (gases, particles, and cloud droplets) before being collected by an appropriately designed optical receiving system.

An electrical current pulse sensor may also be used to detect airborne particles. When a particle hits a metal electrode that is grounded, electrostatic charges are transferred between the particle and the electrode. As a result, an electrical current pulse is generated in the measurement system. The number of the signal pulse represents the number of particles in the sample, and the magnitude of the measured signal is linearly proportional to the square of the particle's diameter. Thus, the pulse may be used to both count and size airborne particles, at a single particle level.

Laser scattering is another sensing technique used for measuring of airborne particles. Laser scattering is widely used to measure airborne concentration of pollutants that are 100 nm or larger in size. A controlled airflow is created inside the sensor by means of a fan. Environmental particular matter travels inside the sensor from an inlet to an outlet, carried by the airflow. Particles in the airstream pass through a focused laser beam, causing light scattering. The scattered light is then detected by a photodiode and converted to a mass and number concentration output.

For gaseous chemicals, an electrochemical sensor, metal oxide sensor, or optical sensor may be used. An electrochemical sensor operates based on a chemical reaction between gases in the air and an electrode inside a liquid inside a sensor. In a metal oxide sensor, gases in the air react on the sensor surface and modify its resistance. Optical sensors detect gases by measuring their absorption of infrared light. These types of sensors are widely used for detection of airborne gases such as carbon monoxide, carbon dioxide, nitrous oxide, nitrogen dioxide, sulfur dioxide, and ozone.

For volatile organic chemicals, such as essential oils, a photo ionization detector may be used. A photo ionization detector ionizes volatile organic compounds and measures the resulting electric current.

Optionally, measuring sensor 22 is an electronic nose, and/or uses analytical techniques used by electronic noses. An electronic nose is a device that uses one or more analytical techniques and machine learning to measure components of an airborne mixture of chemicals and determine an odor generated by the airborne mixture. Electronic noses may incorporate various types of sensors, including the sensors listed above, metal oxide semiconductor (MOS) sensors, colorimetric optical sensors, dye polymer sensors, receptor-based arrays, surface acoustic wave (SAW) sensors, modular gas sensors, fluorescence optical sensors, carbon black-polymers, conducting polymers, and quartz microbalance (QMB) sensors.

The foregoing list of sensors is not exhaustive, and any suitable sensor may be incorporated into the described environment.

Processing circuitry 20 is connected to the measuring sensor 22. Processing circuitry 20 may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network.

The computer readable program instructions may execute entirely on the processing circuitry 20, partly on the processor, as a stand-alone software package, partly on the processing circuitry 20 and partly on a remote computer or entirely on the remote computer or server. In the latter scenario, the remote computer may be connected to the processing circuitry 20 through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Processing circuitry 20 receives measuring data from the measuring sensor 22, and calculates the rate of increase of the airborne concentration of the first chemical 14. When the processing circuitry 20 determines that the rate of concentration of the first chemical 14 has increased beyond a predetermined rate, it issues a notification. As discussed above, the predetermined rate is set based, inter alia, on environmental conditions, such as strength of air flow. The predetermined rate may be adapted to historical data for measuring the concentration of the first chemical 14. As discussed above, in situations when a patch 16 is attached to the user's clothing or body, measuring sensor 22 is configured to measure airborne concentration of the second chemical, as well. In such situations, the processing circuitry 20 is configured to issue the notification only when the airborne concentration of the first chemical increases at a rate that exceeds the increase in concentration of the second chemical by a predetermined value.

The notification may be an audible notification, such as an alarm sound, a visual notification, such as a flashing red light, or an electronic notification, such as an SMS or an email, or any combination thereof. The notification may include a message to the user, such as an instruction to adjust a fit of the facemask, or an instruction to modulate a loudness of vocalization or a force of exhaling. These notifications thus instruct the user to correct the behaviors that caused the rapid increase of airborne concentration of the first chemical 14. The notification may also, for example, include an indication that the safety of the room has been compromised, and/or an instruction to clear the room.

Figure 5:
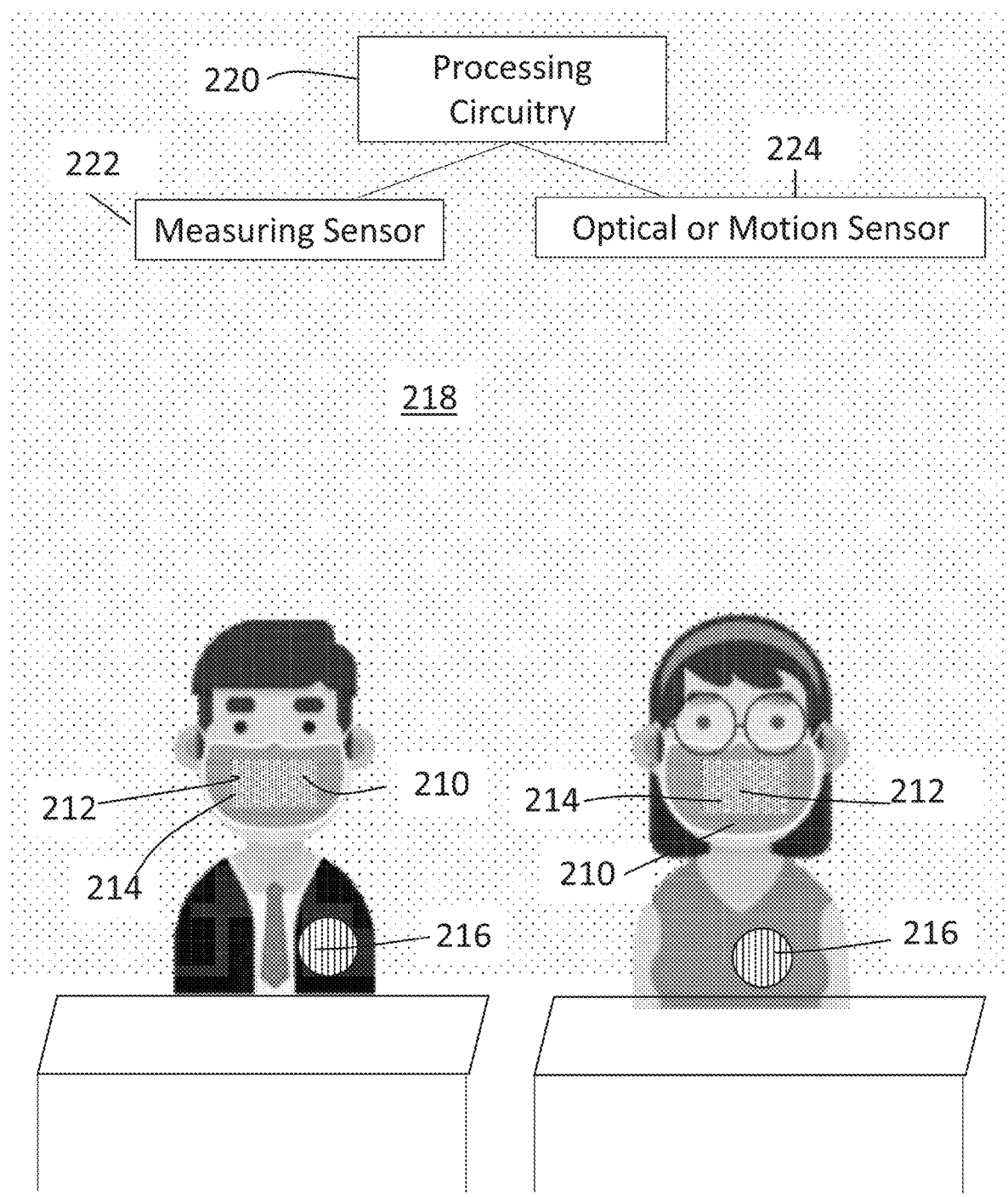
FIG. 5 is a schematic depiction of a system for automatic tracing of exhaled particles with multiple users, according to embodiments of the present disclosure.

FIG. 5 schematically depicts components of a kit that is used to measure measuring a rate of increase of exhaled airborne particles, with multiple users. Elements of the environment of FIG. 5 are similar to those of FIG. 4, and are assigned similar reference numerals, except that they begin with "2." Each user wears a mask 210, including layer 212 with first chemical 214. The users also optionally wear a patch 216. Airborne particles of the first chemical 214 are represented by dots 218, and are measured by measuring sensor 222. The environment of FIG. 5 also includes an optical or motion sensor 224. The optical or motion sensor 224 is used to measure the number of persons in a room. In certain embodiments, the processing circuitry 220 is programmed to set the predetermined rate based on the number of users in the room. For example, to determine that one of the users in the room is spreading airborne particles at an unusually high rate, it is necessary to adjust the predetermined rate to account for a larger number of users. In other embodiments, the predetermined rate is left unchanged regardless of the number of users in the room. For example, if the objective is to determine whether a large cumulative concentration of airborne particles has been released into the room, which may compromise the safety of the room, it is less relevant whether those particles came from one user or from multiple users.

Figure 6:
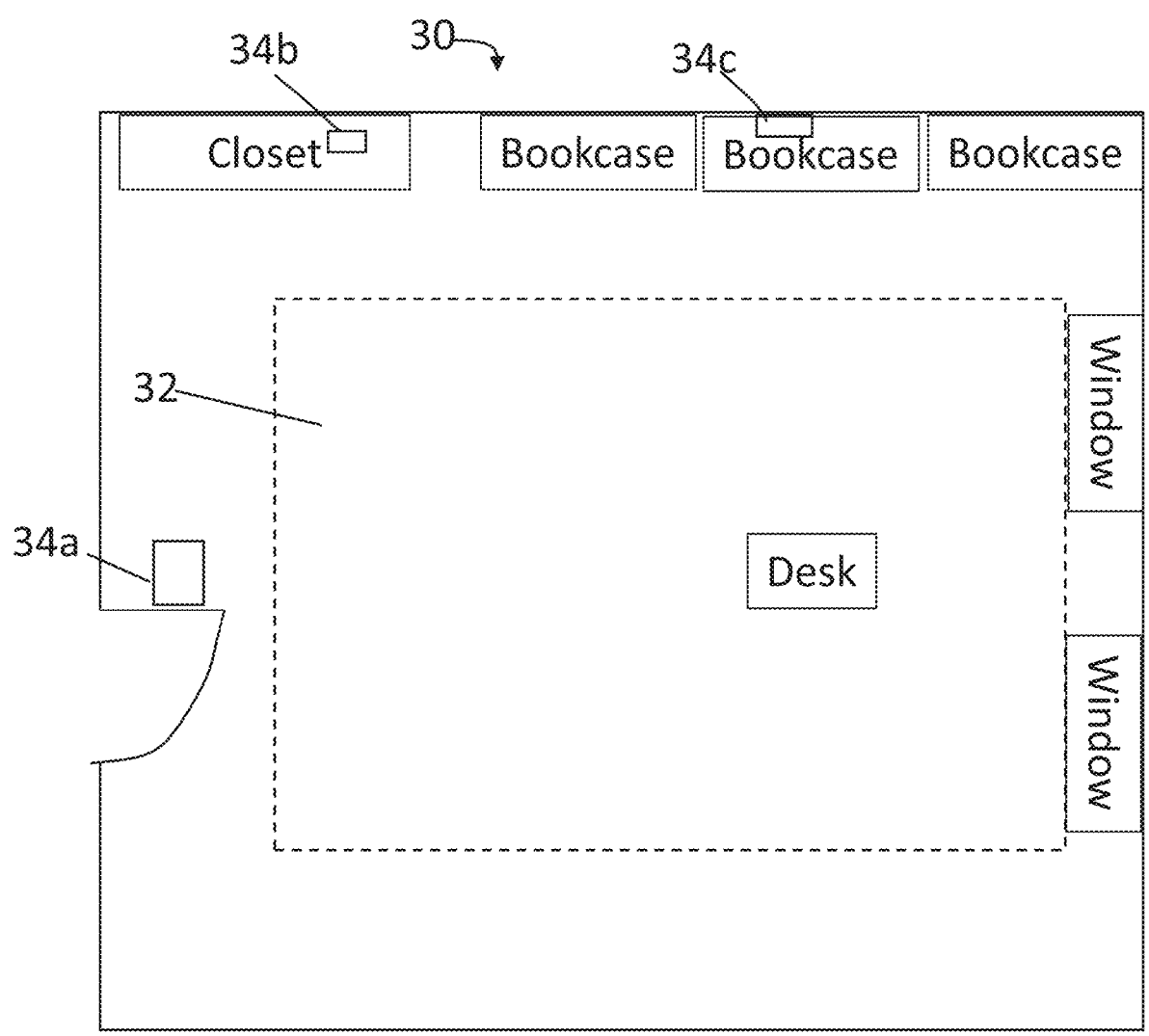
FIG. 6 is a schematic depiction of an environment in which a sensor for measuring airborne concentration of a chemical may be installed, according to embodiments of the present disclosure.

FIG. 6 depicts a layout of a room 30 in which a sensor 22 may be installed. In the illustration of FIG. 6, room 30 is an office, and includes a closet, bookcases, windows, and a desk. A user typically would spend almost all of his time in the office in central area 32. Central area 32 may also be referred to herein as a delineated space for user movement. As such, a suitable placement for sensor 22 would be a peripheral location of the office, such as location 34a, 34b, or 34c. Placement of the sensor in a peripheral area would minimize the likelihood of causing a "false positive" notification due to a user breathing very close to the sensor. Distancing the sensor from the delineated space for user movement may also be accomplished, for example, by mounting the sensor on the ceiling.

It is expected that during the life of a patent maturing from this application many chemicals, sensors, and analytical techniques will be developed that are suitable for the functions described herein, and the scope of the terms chemical and sensor is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is the intent of the applicant(s) that all publications, patents and patent applications referred to in this specification are to be incorporated in their entirety by reference into the specification, as if each individual publication, patent or patent application was specifically and individually noted when referenced herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A kit, comprising:
   at least one facemask configured to cover a respective user's mouth and nose, the at least one facemask containing at least one layer impregnated with a first chemical, and wherein, when the at least one facemask covers the respective user's mouth and nose, airborne particles of the first chemical are released from the at least one layer through the user's breathing;
   a sensor configured to measure airborne concentration of the first chemical; and
   a processing circuitry configured to receive the outputs of the sensor, to calculate a change in airborne concentration of the first chemical, and to issue a notification when the airborne concentration of the first chemical increases at above a predetermined rate.

2. The kit of claim 1, wherein the first chemical adheres to exhaled aerosol droplets with a diameter less than 5 μm.

3. The kit of claim 1, wherein the first chemical is odorless to a human olfactory system.

4. The kit of claim 1, wherein the first chemical emits an odor that is recognizable to a human olfactory system at concentrations above an odor detection threshold, and is impregnated at a sufficiently low concentration such that the airborne particles are released from the at least one facemask at a concentration below the odor detection threshold.

5. The kit of claim 1, wherein the first chemical is a monosaccharide, a disaccharide, a polysaccharide, or a sugar alcohol.

6. The kit of claim 1, wherein the sensor is configured to measure airborne concentration of the first chemical based on one or more of gas chromatography, mass spectrometry, Raman spectroscopy, time of flight analysis, electrical current pulse sensing, or laser scattering.

7. The kit of claim 1, further comprising a patch impregnated a second chemical and attachable to a user's clothing or body, and wherein, when the patch is worn by the user, the sensor is configured to measure airborne concentration of the second chemical, and wherein the processing circuitry is configured to issue the notification only when the airborne concentration of the first chemical increases at a rate that exceeds the increase in concentration of the second chemical by a predetermined value.

8. The kit of claim 1, wherein the sensor is installed in a location having a delineated space for user movement, at a predetermined minimum distance from said delineated space.

9. The kit of claim 1, further comprising a motion sensor or optical sensor, wherein the motion sensor or optical sensor is configured to determine a number of users in a room, and wherein the processing circuitry is configured to set the predetermined rate based on the number of users.

10. The kit of claim 1, wherein the notification includes an instruction to the user to adjust a fit of the at least one facemask.

11. The kit of claim 1, wherein the notification includes an instruction to the user to modulate a loudness of vocalization or a force of exhaling.

12. A method comprising:
    measuring airborne concentration of a first chemical, wherein the first chemical is released from at least one layer of at least one facemask impregnated with said first chemical due to a respective user's breathing when wearing the at least one facemask;
    calculating a change in airborne concentration of the first chemical; and
    issuing a notification when the airborne concentration of the first chemical increases at above a predetermined rate.

13. The method of claim 12, wherein the first chemical adheres to exhaled aerosol droplets with a diameter less than 5 μm, and a measuring step comprises measuring airborne concentration of aerosolized particles of the first chemical.

14. The method of claim 12, wherein a measuring step comprises measuring airborne concentration of the first chemical based on one or more of gas chromatography, mass spectrometry, Raman spectroscopy, time of flight analysis, electrical current pulse sensing, or laser scattering.

15. The method of claim 12, further comprising measuring airborne concentration of a second chemical, wherein the second chemical is impregnated on a patch that is attachable to the user's clothing or body, calculating a change in airborne concentration of the second chemical, and issuing the notification only when the airborne concentration of the first chemical increases at a rate that exceeds the increase in concentration of the second chemical by a predetermined value.

16. The method of claim 12, wherein a measuring step is performed at a predetermined minimum distance from a delineated space for user movement.

17. The method of claim 12, further comprising determining a number of users in a room with a motion sensor or optical sensor, and setting the predetermined rate based on the number of users.

18. The method of claim 12, wherein the issuing a notification comprises instructing the user to adjust a fit of the at least one facemask.

19. The method of claim 12, wherein the issuing a notification comprises instructing the user to modulate a loudness of vocalization or a force of exhaling.

* * * * *